(12) United States Patent
Mansi et al.

(10) Patent No.: US 12,059,219 B2
(45) Date of Patent: Aug. 13, 2024

(54) ASSISTED STEERING OF INTRACARDIAC ECHOCARDIOGRAM CATHETERS

(71) Applicant: SIEMENS HEALTHINEERS AG, Forchheim (DE)

(72) Inventors: Tommaso Mansi, Plainsboro, NJ (US); Young-Ho Kim, West Windsor, NJ (US); Ankur Kapoor, Plainsboro, NJ (US); Jarrod Collins, Wilsonville, OR (US); Rui Liao, Princeton Junction, NJ (US); Thomas Pheiffer, Philadelphia, PA (US)

(73) Assignee: Siemens Healthineers AG, Forchheim (DE)

( * ) Notice: Subject to any disclaimer, the term of this patent is extended or adjusted under 35 U.S.C. 154(b) by 431 days.

(21) Appl. No.: 16/949,761

(22) Filed: Nov. 13, 2020

(65) Prior Publication Data

US 2021/0145412 A1 May 20, 2021

Related U.S. Application Data

(60) Provisional application No. 62/935,841, filed on Nov. 15, 2019.

(51) Int. Cl.
*A61B 34/10* (2016.01)
*A61B 8/00* (2006.01)
(Continued)

(52) U.S. Cl.
CPC ............ *A61B 34/30* (2016.02); *A61B 8/0883* (2013.01); *A61B 8/12* (2013.01); *A61B 8/4254* (2013.01);
(Continued)

(58) Field of Classification Search
CPC ... A61B 34/10; A61B 34/20; A61B 2034/301; A61M 25/0133
See application file for complete search history.

(56) References Cited

U.S. PATENT DOCUMENTS 5,417,210 A * 5/1995 Funda ................. B25J 17/0275
600/109
7,666,191 B2 2/2010 Orban et al.
(Continued)

FOREIGN PATENT DOCUMENTS

EP       1906858 A1 *  4/2008  ........... A61B 1/2676
WO  WO-2019183141 A1 *  9/2019  ........... B25J 13/088

OTHER PUBLICATIONS

U.S. Appl. No. 16/907,675, filed Jun. 22, 2020, entitled "Dual Manipulation for Robotic Catheter Systems," not yet published.
(Continued)

*Primary Examiner* — Rochelle D Turchen

(57) ABSTRACT

Systems and method for assisted catheter steering are provided. Instructions for steering a catheter within a patient are received. A graph defining paths between a plurality of configurations of a robotic catheter navigation system is constructed based on the received instructions. Each of the plurality of configurations are associated with a respective view of the patient. A path is determined in the graph to a target configuration of the plurality of configurations of the robotic catheter navigation system. The catheter is automatically steered within the patient based on the determined path in the graph to recover the respective view of the patient associated with the target configuration.

15 Claims, 9 Drawing Sheets

(51) Int. Cl.
*A61B 8/08* (2006.01)
*A61B 8/12* (2006.01)
*A61B 34/30* (2016.01)
*A61M 25/01* (2006.01)
*G06N 3/045* (2023.01)
*G06N 7/01* (2023.01)
*A61B 17/00* (2006.01)
*A61B 34/20* (2016.01)

(52) U.S. Cl.
CPC ............... *A61B 8/461* (2013.01); *A61B 8/54* (2013.01); *A61B 34/10* (2016.02); *A61M 25/0133* (2013.01); *G06N 3/045* (2023.01); *G06N 7/01* (2023.01); *A61B 2017/00207* (2013.01); *A61B 34/20* (2016.02); *A61B 2034/301* (2016.02)

(56) References Cited

U.S. PATENT DOCUMENTS

| | | | |
|---|---|---|---|
| 7,699,855 B2 | 4/2010 | Anderson et al. | |
| 7,886,743 B2 | 2/2011 | Cooper et al. | |
| 8,206,406 B2 | 6/2012 | Orban et al. | |
| 8,220,468 B2 | 7/2012 | Cooper et al. | |
| 8,998,799 B2 | 4/2015 | Orban et al. | |
| 8,998,930 B2 | 4/2015 | Orban et al. | |
| 2005/0020911 A1* | 1/2005 | Viswanathan | A61B 34/70 600/424 |
| 2007/0296825 A1* | 12/2007 | Ito | G06F 3/011 348/222.1 |
| 2016/0361129 A1 | 12/2016 | Morrissette et al. | |
| 2016/0367328 A1 | 12/2016 | Dachs et al. | |
| 2018/0177561 A1* | 6/2018 | Mintz | A61B 5/107 |
| 2019/0038282 A1 | 2/2019 | Shelton, IV et al. | |
| 2020/0060646 A1 | 2/2020 | Lindenroth et al. | |
| 2020/0061339 A1 | 2/2020 | Lindenroth et al. | |
| 2020/0237453 A1 | 7/2020 | Anglese | |
| 2020/0261167 A1 | 8/2020 | Anglese | |

OTHER PUBLICATIONS

U.S. Appl. No. 16/809,067, filed Mar. 4, 2020, entitled "Mechanically-Decoupled Actuation for Robotic Catheter System," not yet published.

Loschak et al., "Predictive Filtering in Motion Compensation with Steerable Cardiac Catheters," 2017, IEEE International Conference on Robotics and Automation (ICRA), 8 pgs.

Kim et al., "Towards Automatic Manipulation of Intra-cardiac Echocardiography Catheter," 2020, IEEE Transaction on Medical Robotics and Bionics, 12 pgs.

Loschak et al., Algorithms for Automatically Pointing Ultrasound Imaging Catheters, 2016, IEEE Transactions on Robotics, 11 pgs.

Stereotaxis, "Stereotaxs V-Drive Robotic Navigation System," 2020, retrieved online from http://www.stereotaxis.com/products/#!/vdrive, 6 pgs.

U.S. Appl. No. 17/033,297, filed Sep. 25, 2020, entitled "Holder Facility for Holding a Medical Instrument" not yet published.

* cited by examiner

ASSISTED STEERING OF INTRACARDIAC ECHOCARDIOGRAM CATHETERS

CROSS-REFERENCE TO RELATED APPLICATIONS

This application claims the benefit of U.S. Provisional Application No. 62/935,841, filed Nov. 15, 2019, the disclosure of which is incorporated herein by reference in its entirety.

TECHNICAL FIELD

The present invention relates generally to assisted steering of catheters, and in particular to assisted steering of ICE (intracardiac echocardiogram) catheters for performing an ICE procedure.

BACKGROUND

ICE (intracardiac echocardiogram) is an increasingly popular imaging modality capable of generating high-resolution real-time images of cardiac structures of a patient. ICE has become an important part of cardiac electrophysiology, structural heart interventions, and other interventional cardiac procedures. Compared to transthoracic echocardiograms (TTE), transesophageal echocardiography (TEE), and other common cardiac ultrasound imaging techniques, ICE generates higher quality images, does not require that the patient undergo general anesthesia, and enables direct navigation of ICE catheters by cardiologists.

While ICE provides a number of advantages over other imaging techniques, ICE imaging remains a challenge. For instance, learning how to optimally manipulate the ICE catheter, recognize what is being imaged, and navigate the ICE catheter towards an anatomical object of interest involves a steep learning curve. Furthermore, the relatively small field of view of the ICE catheter prevents a therapy catheter or other device from being maintained in the field of view, thus preventing real-time and continuous control of the procedure. Additionally, cardiologists are unable to operate both the ICE catheter and a therapy catheter, thereby requiring support from a second operator.

BRIEF SUMMARY OF THE INVENTION

In accordance with one or more embodiments, systems and methods for assisted catheter steering are provided. Systems and method for assisted catheter steering are provided. Instructions for steering a catheter within a patient are received. A graph defining paths between a plurality of configurations of a robotic catheter navigation system is constructed based on the received instructions. Each of the plurality of configurations are associated with a respective view of the patient. A path is determined in the graph to a target configuration of the plurality of configurations of the robotic catheter navigation system. The catheter is automatically steered within the patient based on the determined path in the graph to recover the respective view of the patient associated with the target configuration.

In one embodiment, each of the plurality of configurations define a respective position and orientation of the catheter for generating the respective view of the patient. The position of the catheter is defined by a translation parameter and the orientation of the catheter is defined by rotation, anterior/posterior, and left/right parameters.

In one embodiment, the graph is constructed by, for each respective configuration of the plurality of configurations, determining whether the respective configuration is the same as a prior configuration, in response to determining that the respective configuration is not the same as the prior configuration, adding a new vertex representing the respective configuration to the graph, and connecting the new vertex to one or more existing vertices of the graph based on a distance threshold. In one embodiment, the path in the graph to the target configuration of the plurality of configurations of the robotic catheter navigation system is determined in response to a user request In one embodiment, images of views are associated with one or more of the plurality of configurations.

In one embodiment, initial instructions in a coordinate system associated with the patient for steering the catheter are received. The initial instructions in the coordinate system associated with the patient are transformed into a configuration of the robotic catheter navigation system. The initial instructions in the coordinate system associated with the patient may be transformed into the configuration of the robotic catheter navigation system based on a kinematics model of the catheter. In one embodiment, ground truth positions of the catheter are collected and the ground truth positions of the catheter are interpolated to generate unobserved positions of the catheter. Nearest positions between the ground truth positions and the unobserved positions are determined. A mapping function is generated based on the determined nearest positions. The transformed initial instructions are compensated based on the mapping function.

These and other advantages of the invention will be apparent to those of ordinary skill in the art by reference to the following detailed description and the accompanying drawings.

DETAILED DESCRIPTION

The present invention generally relates to methods and systems for assisted steering of ICE (intracardiac echocardiogram) catheters. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

During an ICE procedure, a catheter is navigated within the heart of a patient. A transducer, mounted at the tip of the catheter, transmits ultrasonic signals and receives reflections of the ultrasonic signals to thereby generate high-resolution images from within the heart. To assist in navigating the catheter, a robotic catheter navigation system may be implemented for assisted steering of the catheter to enable a user (e.g., cardiologist, a clinician, or any other user) to manipulate the catheter in all four degrees of freedom (i.e., anterior/posterior tip bending, left/right tip bending, rotation, and translation) needed to fully steer the catheter. One example of such a robotic catheter navigation system is shown in FIG. 1.

Figure 1:
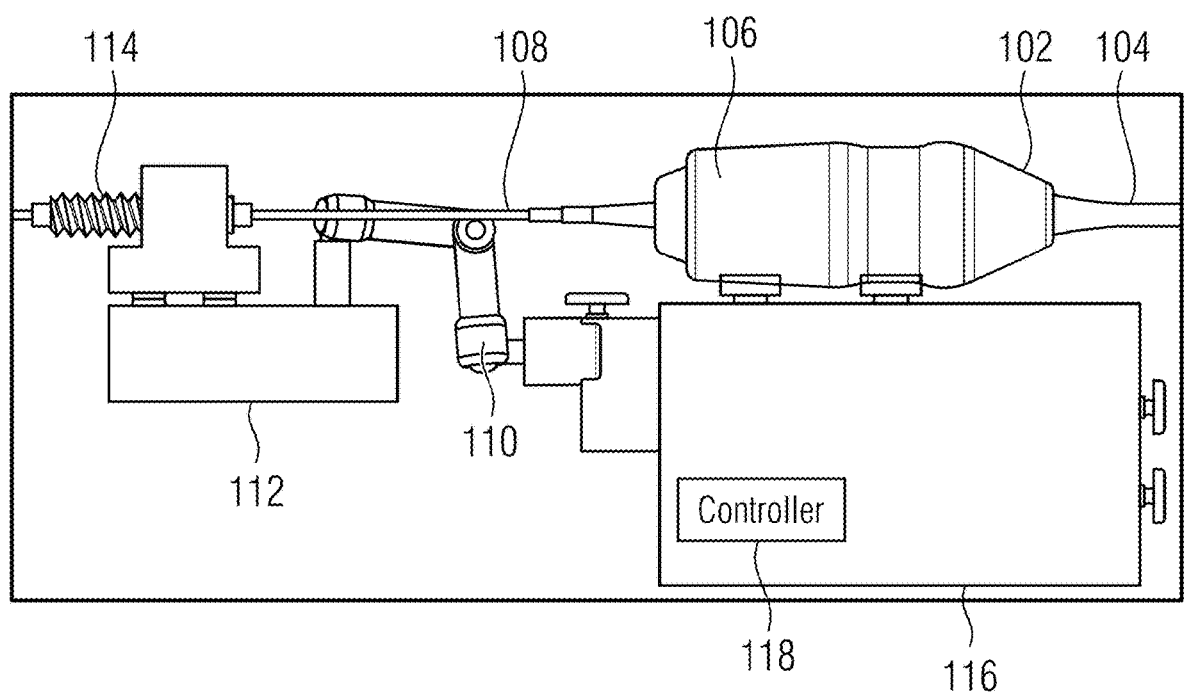
FIG. 1 shows an exemplary robotic catheter navigation system, in accordance with one or more embodiments.

FIG. 1 shows an exemplary robotic catheter navigation system 100, in accordance with one or more embodiments. Robotic catheter navigation system 100 comprises a catheter 108, a base 116, a catheter handle housing 102, an access point base 112, an access point guide 114, and an arm 110. In one embodiment, catheter 108 is an ICE catheter for performing an ICE procedure, but may be any other suitable catheter. Base 116 and catheter handle housing 102 form a handle robot. Access point base 112 and access point guide 114 form an access point robot. Arm 110 connects or links the handle robot to the access point robot. Cable 104 interfaces with an ultrasound device (not shown) for, e.g., image processing, beam forming, displaying the generated image, etc. It should be understood that robotic catheter navigation system 100 of FIG. 1 is exemplary and other configurations of robotic catheter navigation system 100 are possible.

In operation, a user manipulates (e.g., rotates) one or more rotatable knobs 106 to steer catheter 108. In one embodiment, knobs 106 comprise a first knob for bending the tip of catheter 108 in an anterior/posterior direction and a second knob for bending the tip of catheter 108 in a left/right direction. One or more motors (e.g., actuators) in base 116 drive gears in the handle robot to actuate movement (e.g., in the anterior/posterior direction and/or the left/right direction) of catheter 108 by applying pushing or pulling forces on steering wires (not shown) within catheter 108. The access point robot manipulates catheter 108 to provide more direct control of catheter 108 near the insertion point of the patient. The access point robot is configured to translate catheter 108 along its longitudinal axis and/or rotate catheter 108 about its longitudinal axis. Accordingly, robotic catheter navigation system 100 enables steering of catheter 108 is all four degrees of freedom anterior/posterior tip bending, left/right tip bending, rotation, and translation.

Conventionally, steering of catheters for ICE procedure is a challenging task. Advantageously, robotic catheter navigation system 100 comprises a controller 118 implemented in base 116 for assisted catheter navigation in accordance with one or more embodiments described herein. For example, in one embodiment, controller 118 may be configured for automatic view recovery for assisted catheter steering, in accordance with method 200 of FIG. 2. In another embodiment, controller 118 may be configured for intuitive catheter control for assist catheter steering, in accordance with method 400 of FIG. 4. Controller 118 may be implemented using one or more computing devices, such as, e.g., computer 802 of FIG. 8. However, controller 118 may be implemented in any other suitable form, such as, e.g., an application specific integrated circuit, integrated circuit, digital signal processor, field programmable gate array, or any other suitable control device for controlling the motors of the robotic catheter navigation system 100.

Other exemplary robotic catheter navigation systems are described in U.S. patent application Ser. No. 16/809,067, filed Mar. 4, 2020, and U.S. patent application Ser. No. 16/907,675, filed Jun. 22, 2020, the disclosures of which are incorporated herein by reference in their entirety.

Figure 2:
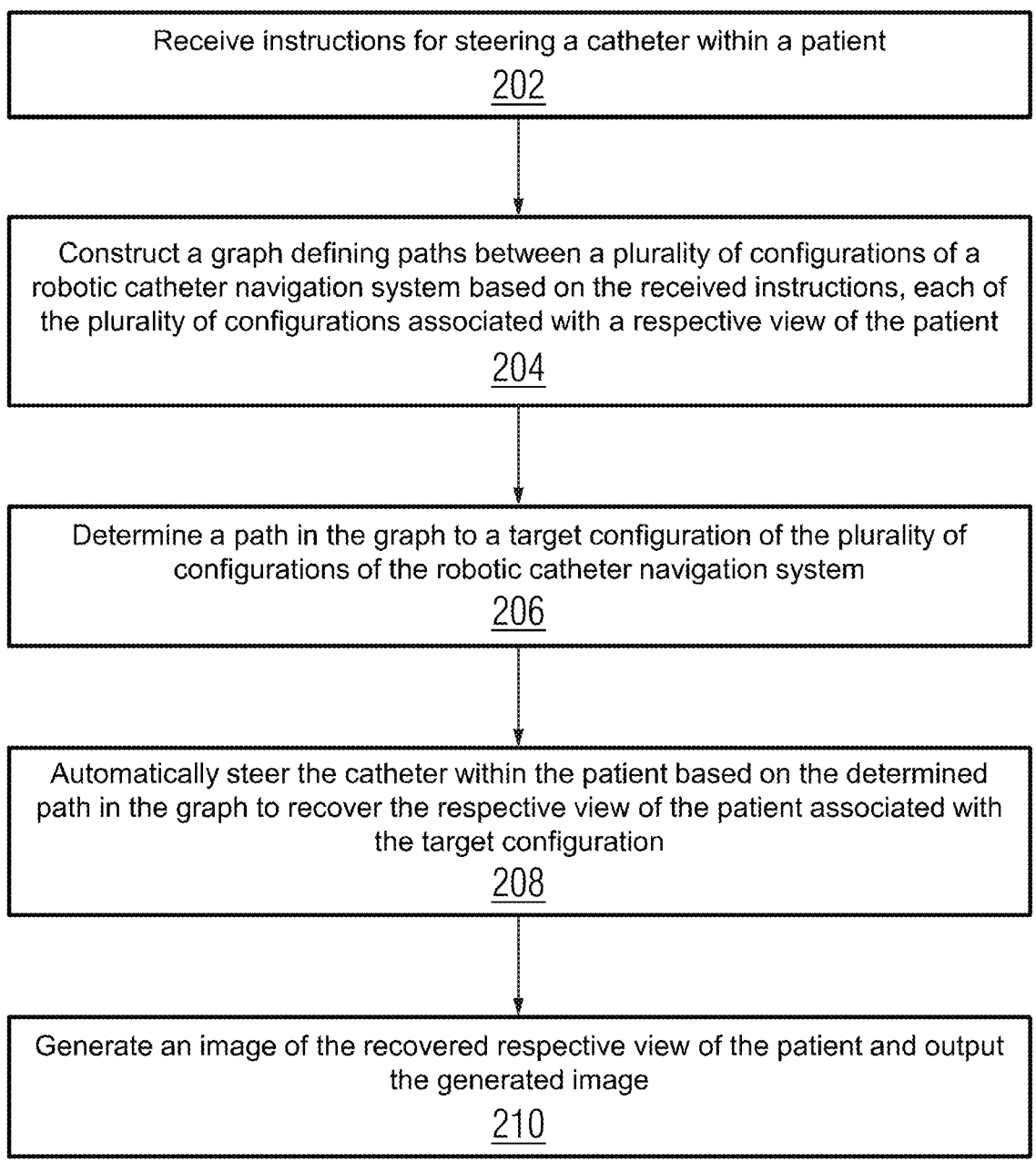
FIG. 2 shows a method for automatic view recovery for assisted catheter steering, in accordance with one or more embodiments.

FIG. 2 shows a method 200 for automatic view recovery for assisted catheter steering, in accordance with one or more embodiments. Method 200 will be described with continued reference to robotic catheter navigation system 100 of FIG. 1. In one example, the steps of method 200 are performed by controller 118 of FIG. 1 for assisted steering of catheter 108. However, the steps of method 200 may be performed by any suitable computing device or devices, such as, e.g., computer 802 of FIG. 8.

At step 202, instructions for steering a catheter within a patient are received. The instructions for steering the catheter may be received from a user (e.g., a cardiologist, a clinician, or any other user). The user may provide the instructions for steering the catheter in any suitable manner. In one embodiment, the user manipulates knobs (e.g., knobs 106) of a robotic catheter navigation system to steer the catheter to define an anterior/posterior tip bending, a left/right tip bending, a rotation, and a translation. However, the user may provide the instructions via any other user input device, such as, e.g., a joystick, an inertial sensor, a camera system, a voice recognition system, etc. In one embodiment, the instructions are received according to method 400 of FIG. 4, described below. In one example, the catheter is catheter 102 of FIG. 1. In one embodiment, the catheter is an ICE catheter comprising an ultrasound transducer for generating views of a heart (or any other anatomical object of interest, such as, e.g., an organ, a bone, etc.) of the patient during an ICE procedure. However, the catheter may be any other suitable catheter.

At step 204, a graph defining paths between a plurality of configurations of a robotic catheter navigation system is constructed based on the received instructions. Each of the plurality of configurations are associated with a respective view of the patient. The plurality of configurations of the robotic catheter navigation system may represent bookmarks or presets of the robotic catheter navigation system to the various views of the patient. In one example, the robotic catheter navigation system is robotic catheter navigation system 100 of FIG. 1.

In one embodiment, the plurality of configurations each define a respective position and orientation of the catheter. The position of the catheter may be defined by a translation parameter and the orientation of the catheter may be defined by rotation, anterior/posterior, and left/right parameters. The parameters are defined relative to a home position and orientation of the catheter, which may be defined by the user of the robotic catheter navigation system. For example, the translation parameter may be a distance and the rotation, anterior/posterior, and left/right parameters may be angles relative to respective parameters of the home position. Accordingly, the configuration of the robotic catheter navigation system defines the position and the orientation of the catheter in four degrees of freedom.

The graph may be constructed as a topological graph g(V,E), where V denotes vertices representing the plurality of configurations $q_i$ and E denotes edges representing paths $(q_i, q_j)$ between the plurality of configurations $q_i$. To construct graph g(V,E), as instructions for steering the catheter are received (at step 202), the catheter moves within the patient and a plurality of configurations $q_n$ are saved. Each configuration $q_n$ may be saved in response to input from the user or may be automatically saved (e.g., at predefined time intervals). For each configuration cm, if configuration cm is not the same as the prior configuration $q_{prior}$, a new vertex of g is inserted representing configuration $q_n$ and the new vertex is connected to existing vertices of g having a distance that satisfies (e.g., is less than) a density parameter threshold $\in$. The distance between vertices may be calculated as a Euclidean distance (assuming 1 mm≡1°) or any other suitable distance metric. In one embodiment, the value of the density parameter threshold E is 1. However, the density parameter threshold $\in$ may be set to any other suitable value.

In one embodiment, images of views may be associated with one or more of the plurality of configurations. The plurality of configurations may therefore be represented by their associated view to create a library V of the views, where V=$(q_1', \ldots, q_m')$, q' is the configuration, and m is the number of saved views.

In one embodiment, if anatomical knowledge of the patient is available, for example through an initial 360 degree sweep and anatomy reconstruction or through pre-operative data, one or more of the plurality of configurations of the robotic catheter navigation system may be automatically calculated based on such anatomical knowledge without the user having to navigate the catheter to that configuration. In another embodiment, if anatomical knowledge of the patient is not available, anatomical knowledge can be progressively captured during an imaging session. An artificial intelligence based image recognition algorithm with active perception may then be employed to enable the catheter to discover anatomical information of the anatomy of interest and the configuration of the robotic catheter navigation system may be automatically calculated based on the discovered anatomical information without the user having to navigate the catheter to that configuration.

At step 206, a path in the graph to a target configuration of the plurality of configurations of the robotic catheter navigation system is determined. The target configuration may be received as user input from the user. For example, the user may select one of the plurality of configurations as the target configuration. In another example, the user may select a view from the library V of the views, and the configuration associated with the selected view is the target configuration.

The path in the graph is determined from a start configuration $q_s$ (which is the current configuration $q_n$) to the target configuration $q_t$. Since each of the plurality of configurations is already represented in graph g, a search algorithm is applied to identify a sequence of edges that forms the path between $q_s$ and $q_t$. In one embodiment, the search algorithm is a discrete A* search algorithm, but may be any other suitable algorithm.

At step 208, the catheter is automatically steered within the patient based on the determined path in the graph to recover the respective view of the patient associated with the target configuration. The trajectory from the current position of the catheter is automatically generated based on the path in the graph.

At step 210, optionally, an image of the recovered respective view of the patient is generated and the generated image is output. For example, the generated image can be output by displaying the generated image on a display device of a computer system, storing the generated image on a memory or storage of a computer system, or by transmitting the generated image to a remote computer system.

In one embodiment, steps 206, 208, and optionally 210 may be repeated any number of times (e.g., as requested by the user) to repeatedly recover other views of the patient associated with other target configurations of the plurality of configurations.

Figure 3:
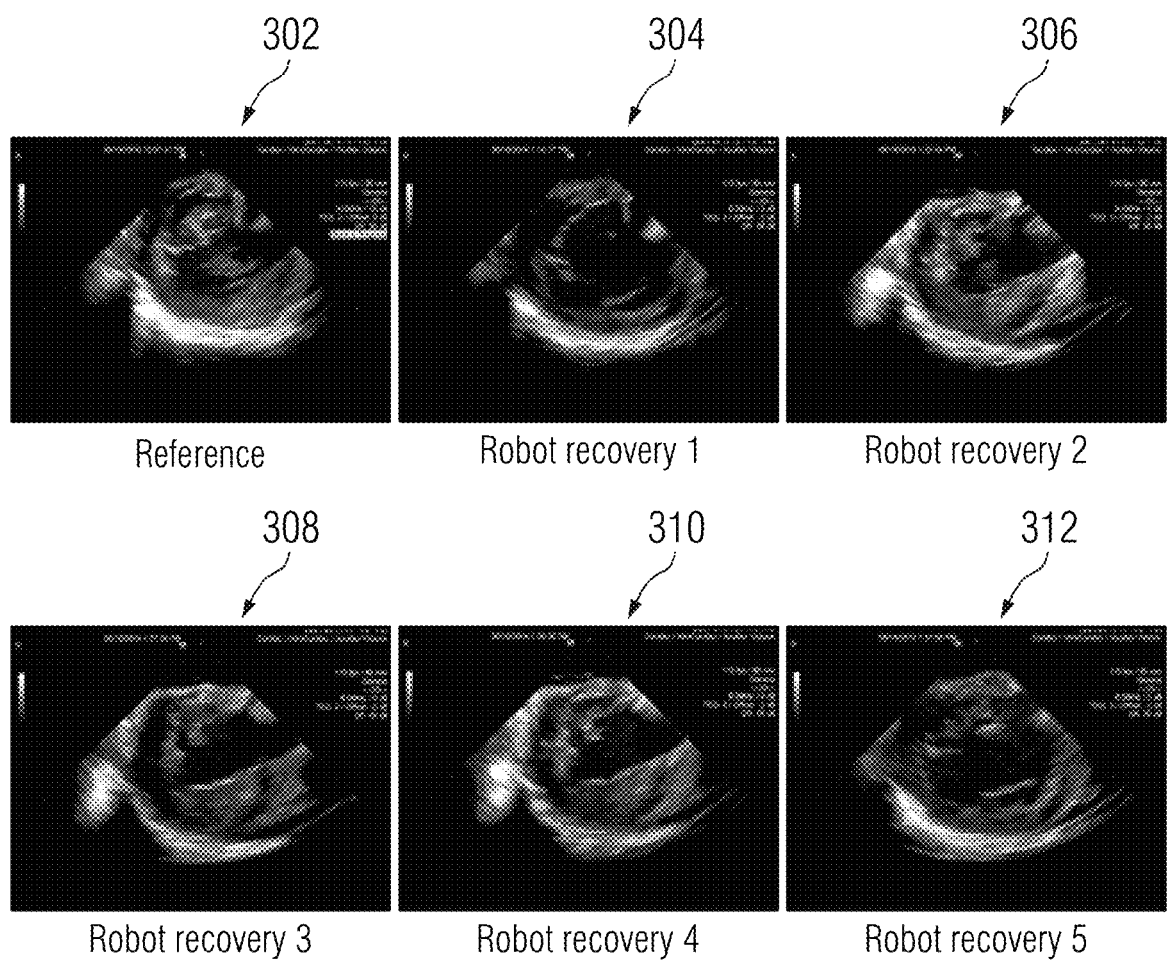
FIG. 3 shows images comparing a reference image with various recovered images recovered in accordance with one or more embodiments.

Method 200 was experimentally validated. FIG. 3 shows images 300 of results of the experimental validation comparing a reference image with various recovered images recovered in accordance with one or more embodiments. Reference image 302 represents an image of a view of the mitral valve of a patient acquired by an user manually steering a robotic catheter navigation system. Robot recovery images 304-312 represent recovered views recovered in accordance with method 200 of FIG. 2. Robot recovery images 304-312 were found to have an average position error of 4.6 mm±2.1 mm and an average orientation error of 4.6°±3.0°.

Figure 4:
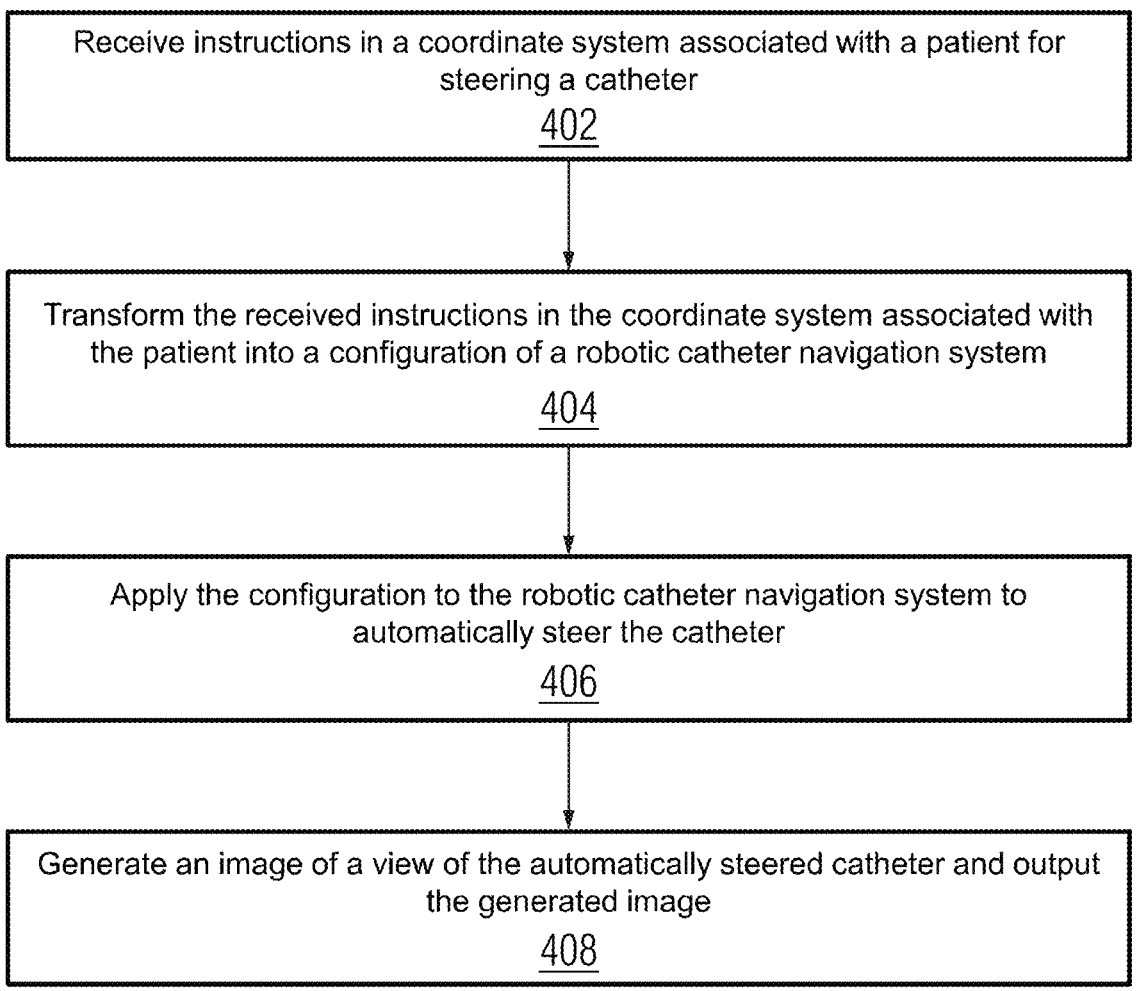
FIG. 4 shows a method for intuitive catheter control for assisted catheter steering, in accordance with one or more embodiments.

FIG. 4 shows a method 400 for intuitive catheter control for assisted catheter steering, in accordance with one or more embodiments. Method 400 will be described with continued reference to robotic catheter navigation system 100 of FIG. 1. In one embodiment, the steps of method 400 are performed by controller 118 of FIG. 1 for assisted steering of catheter 108. However, the steps of method 400 may be performed by any other suitable computing device or devices, such as, e.g., computer 802 of FIG. 8.

At step 402, instructions in a coordinate system associated with a patient for steering a catheter are received. The coordinate system associated with the patient may be a coordinate system associated with a heart of the patient or any other anatomical object of interest of the patient. The coordinate system associated with the patient may be an (X,Y,Z) Cartesian coordinate system. In one example, the catheter is catheter 102 of FIG. 1. In one embodiment, the catheter is an ICE catheter comprising an ultrasound transducer for generating images of the anatomical objects of interest of the patient for performing an ICE procedure. However, the catheter may be any other suitable catheter.

The instructions may be received from a user (e.g., cardiologist, clinician, or any other user). In order to provide the instructions in the coordinate system associated with the patient, the user provides the instructions via a user input device, instead of manipulating knobs of a robotic catheter navigation system. In one example, the user input device is a joystick having four degrees of freedom. In another example, the user input device is an inertial sensor to estimate movement in four degrees of freedom. The inertial sensor may be implemented within a device, such as, e.g., a joystick, a tablet, a phone, etc. Alternatively, the inertial sensor may be attached to the user (e.g., to the arm of the user) and turned on and off through, e.g., a button, a specific gesture, voice control, etc. In another example, the user input device is a camera system comprising one or more cameras, such as, e.g., an RGBD (red green blue depth) camera or a stereo camera. Such a camera system may be used to recognize hand gestures of the user to control the catheter. For example, hand translation along the an (X,Y,Z) coordinate system of the cameras, along with hand rotation with respect to the arm axis, can be recognized and directly mapped to catheter controls. A simple gesture (e.g., a hand snap) may change the control mode. A hand sweep (e.g., left to right) may be used to switch views. In another embodiment, the user input device is a voice control device. The user may provide instructions through voice based commands, such as, e.g., rotate, up, down, left, right, backwards, forward, next view, previous view, mitral valve, etc. Such voice based commands are connected to related catheter controls. In this manner, the catheter may be controlled through discrete actions whose amplitude can be adjusted through voice based commands. Other user input devices are also contemplated.

At step 404, the received instructions in the coordinate system associated with the patient are transformed into a configuration of a robotic catheter navigation system. In one example, the robotic catheter navigation system is robotic catheter navigation system 100 of FIG. 1.

In one embodiment, the configuration of the robotic catheter navigation system comprises a translation parameter defining a position of the catheter and rotation, anterior/posterior, and left/right parameters defining the orientation of the catheter. The parameters are defined relative to a home position and orientation of the catheter. For example, the translation parameter may be a distance and the rotation, anterior/posterior, and left/right parameters may be angles relative to the home position. Accordingly, the configuration of the robotic catheter navigation system defines the position and the orientation of the catheter in four degrees of freedom.

In one embodiment, the configuration of the robotic catheter navigation system comprises a configuration of left/right parameter $\phi_1$, anterior/posterior parameter $\phi_2$, rotation parameter $\phi_3$, and distance parameter $d_4$ of the robotic catheter navigation system for rotating the catheter. To transform the received instructions in the coordinate system associated with the patient to a configuration of the robotic catheter navigation system for rotating the catheter, a kinematics model is applied to model the bending geometry of the catheter. The kinematics model comprises a forward kinematics model f of the catheter and an inverse kinematics model $f^{-1}$ of the catheter, which are estimated during a prior offline stage such that rotation along the catheter axis $\phi=f(\phi_1, \phi_2, \phi_3, d_4)$. The user directly defines the rotation $\phi$ using the user input device and the corresponding parameters $\phi_1$, $\phi_2$, $\phi_3$, $d_4$ are estimated by applying the inverse kinematics model $f^{-1}$ of the catheter. Accordingly, the user performs the catheter sweep for rotating the catheter without having to perform the manipulations for defining parameters $\phi_1$, $\phi_2$, $\phi_3$, $d_4$ directly on robotic catheter navigation system.

The forward and inverse kinematics model of the catheter may be any suitable model of the kinematics of the catheter. In one embodiment, model parameter identification may be performed to handle more complex catheter kinematics due to the slack of the catheter due to the push/pull mechanism.

Figure 5:
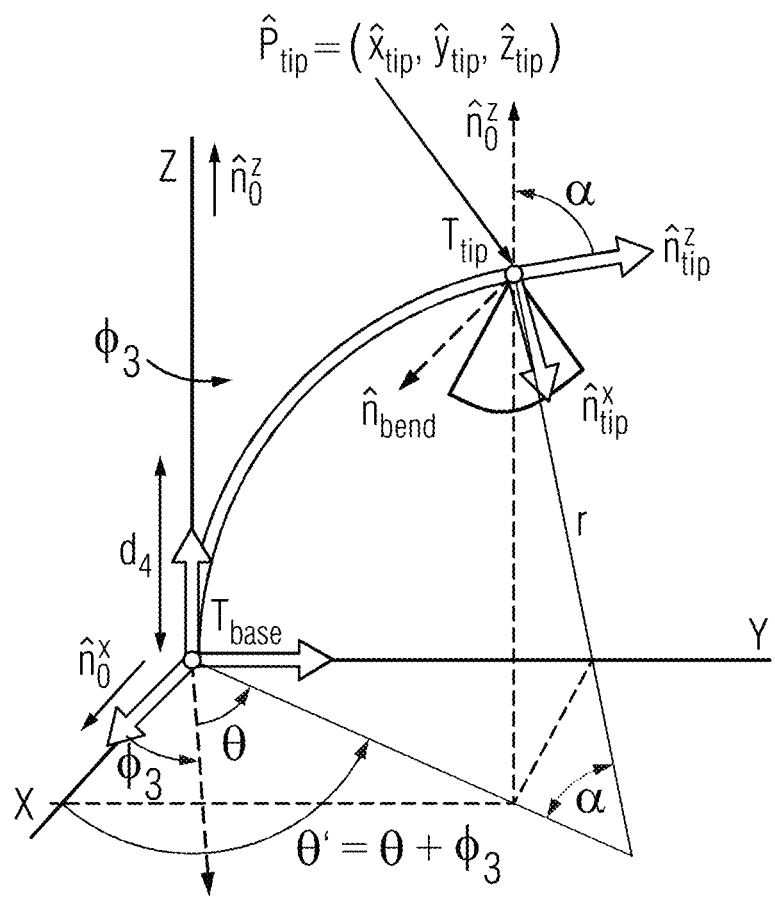
FIG. 5 shows a forward kinematics model of a catheter and an inverse kinematics model of the catheter, in accordance with one or more embodiments.

FIG. 5 shows catheter bending geometry 500, in accordance with one or more embodiments. $T_{base}$ denotes the base coordinate frame for the bottom of the bending section of the catheter, $T_{tip}$ denotes the catheter tip coordinate frame where the ultrasound array is installed, and $\hat{n}_x^{tip}$ denotes the center of the image facing direction.

The forward kinematics model f may be employed for transforming left/right parameter $\phi_1$, anterior/posterior parameter $\phi_2$, rotation parameter $\phi_3$, and distance parameter $d_4$ to the position $T_{tip}$ of the tip of catheter 502, such that $f(\phi_1, \phi_2, \phi_3, d_4) \ T_{tip}$. As shown in FIG. 5, there exist two configuration parameters: $\theta$ and $\alpha$. $\theta$ is the right handed rotation angle from $\hat{n}_0^x$ (the x-axis of $T_{base}$) and $\alpha$ is the angle of curvature computed from anterior-posterior thread deflection $L_{ap}$ and right-left thread deflection $L_{rl}$. Thread deflections $L_{ap}$ and $L_{rl}$ are computed from $\phi_1$ and $\phi_2$, along with a knob radius $r_{knob}$ as:

$$L_{ap} = \phi_1 \cdot r_{knob} \quad \text{Equation 1}$$

$$L_{rl} = \phi_2 \cdot r_{knob} \quad \text{Equation 2}$$

Then, $\alpha$ may be computed as:

$$\alpha = \sqrt{\left(\frac{L_{ap}}{r_{catheter}}\right)^2 + \left(\frac{L_{rl}}{r_{catheter}}\right)^2} \quad \text{Equation 3}$$

where $r_{catheter}$ is the radius of the catheter.

The remaining components of the forward kinematics model may be computed as follows:

$$\theta = \tan^{-1}\left(\frac{\phi_1}{\phi_2}\right) \quad \text{Equation 4}$$

$$r = \frac{L}{\alpha} \quad \text{Equation 5}$$

$$\hat{x}_{tip} = r(1 - \cos \alpha) \cos \theta \quad \text{Equation 6}$$

$$\hat{y}_{tip} = r(1 - \cos \alpha) \sin \theta \quad \text{Equation 7}$$

$$\hat{z}_{tip} = r \sin \alpha \quad \text{Equation 8}$$

where $\theta$ is the angle between the bending plane (due to $\phi_1$ and $\phi_2$) and the X-Z plane when $\phi_3=0$ and r is the radius of curvature. The catheter tip position $\hat{P}_{tip}$ is calculated from Equations 6-8.

The orientation of the tip can be calculated by the Rodrigues' rotation formula, which is a method for rotating a vector in space, given an axis and an angle of rotation. Let $R(\mu,\beta)$ be the rotation matrix using Rodrigues' rotation formula from the given axis and rotating it by an angle $\beta$ according to the right hand rule. Then, the orientation of the tip is computed by $R(\hat{n}_{bend},\alpha)$, where $\hat{n}_{bend}$ is the vector orthogonal to the bending plane.

Let $T_{tilt}$ be the 4×4 transformation matrix from $\hat{P}_{tip}$ and $R(\hat{n}_{bend},\alpha)$ without the body rotation $\phi_3$ and translation $d_4$. The rotation of $\phi_3$ is $T_{roll}(\phi_3)$. The translation of $d_4$ is $T_{trans}(d_4)$. Then, the overall transformation matrix $T_{ap}$ is given as:

$$T_{tip} = T_{trans}(d_4) \cdot T_{roll}(\phi_3) \cdot T_{tilt} \cdot T_{US} \quad \text{Equation 9}$$

where $T_{US}$ is the constant transformation from the tip of the bending section to the center of the ultrasound images along the catheter axis.

The inverse kinematics model $f^{-1}$ may be employed for transforming the position $T_{ap}$ of the tip of catheter to left/right parameter $\phi_1$, anterior/posterior parameter $\phi_2$, rotation parameter $\phi_3$, and distance parameter $d_4$, such that $f^{-1}(T_{tip}) \rightarrow (\phi_1, \phi_2, \phi_3, d_4)$. The inverse kinematics may be calculated as follows:

$$\alpha = \cos^{-1}(\hat{n}_z^0 \cdot \hat{n}_{tip}^z) \quad \text{Equation 10}$$

$$\theta' = \text{atan2}(\hat{Y}_{tip}, \hat{X}_{tip}) \quad \text{Equation 11}$$

$$\hat{\phi}_3 = \theta' - \text{atan2}(\hat{n}_{tip}^x \times R(\hat{n}_0^x, \alpha), \hat{n}_{tip}^x \cdot R(\hat{n}_0^x, \alpha)) \quad \text{Equation 12}$$

-continued $$\hat{\phi}_1 = \frac{\alpha \cdot r_{catheter} \cdot \cos(\theta)}{r_{knob}} \quad \text{Equation 13}$$

$$\hat{\phi}_2 = \frac{\alpha \cdot r_{catheter} \cdot \sin(\theta)}{r_{knob}} \quad \text{Equation 14}$$

$$d_4 = \hat{z}_{tip} - r \cdot \sin \alpha \quad \text{Equation 15}$$

$\alpha$ is the dot product of $\hat{n}_z^0$ (the z-axis of $T_{base}$) and $\hat{n}_{tip}^z$ (the z-axis of the catheter tip) in Equation 10. $\theta'$ is computed from the catheter tip position $\hat{P}_{tip}$ in Equation 11. $\hat{\phi}_3$ is computed from the angle between $R(\hat{n}_0^x, \alpha)$ (the x-axis of $T_{base}$ rotated by $\alpha$) and the dot product of $\hat{n}_{tip}^x$ (the x-axis of $T_{tip}$) and $R(\hat{n}_0^x, \alpha)$. The computed $\hat{\phi}_1$ and $\hat{\phi}_2$ represent the estimated joint states, which will be compensated for updated real values $\phi_1'$ and $\phi_2'$. $\hat{\phi}_3$ is equal to $\phi_3$ since the computed angle is given from the input. It is assumed that other estimated joint states ($\phi_3$ and $d_4$) are not affected by the non-linearity as the realization of these degrees of freedoms are also detached from catheter bending.

Let $P_{tip} \in \mathbb{R}^3$ be the real position ($x_{tip}$, $y_{tip}$, $z_{tip}$) of the catheter tip. When $\phi_1$ and $\phi_2$ are applied to the kinematics model, the predicted position $\hat{P}_{tip}$ can present large discrepancies with the actual position $P_{tip}$ due to the effects of non-linear elasticity of the bending space. It is assumed that the bending length of the catheter remains constant due to the arc constraints, and the two control knobs (i.e., anterior/posterior and left/right) cover the full working space. Accordingly, only $\hat{P}_{tip}$ and $P_{tip}$ are misaligned.

To increase the accuracy of the kinematics model, a mapping function F is applied to map the model input ($\phi_1$ and $\phi_2$ for $\hat{P}_{tip}$) to the real joint states ($\phi_1'$ and $\phi_2'$ for $P_{tip}$). This mapping function F is applied to both the forward kinematics model and the inverse kinematics model. The mapping function F is defined as follows:

$$\phi_1', \phi_2' = F(\phi_1, \phi_2) \quad \text{Equation 16}$$

The mapping function F: $\phi_1, \phi_2 \rightarrow \phi_1', \phi_2'$ is the mapping function based on correcting the estimated position $\hat{P}_{tip}$ to the real position $P_{tip}$.

Figure 6:
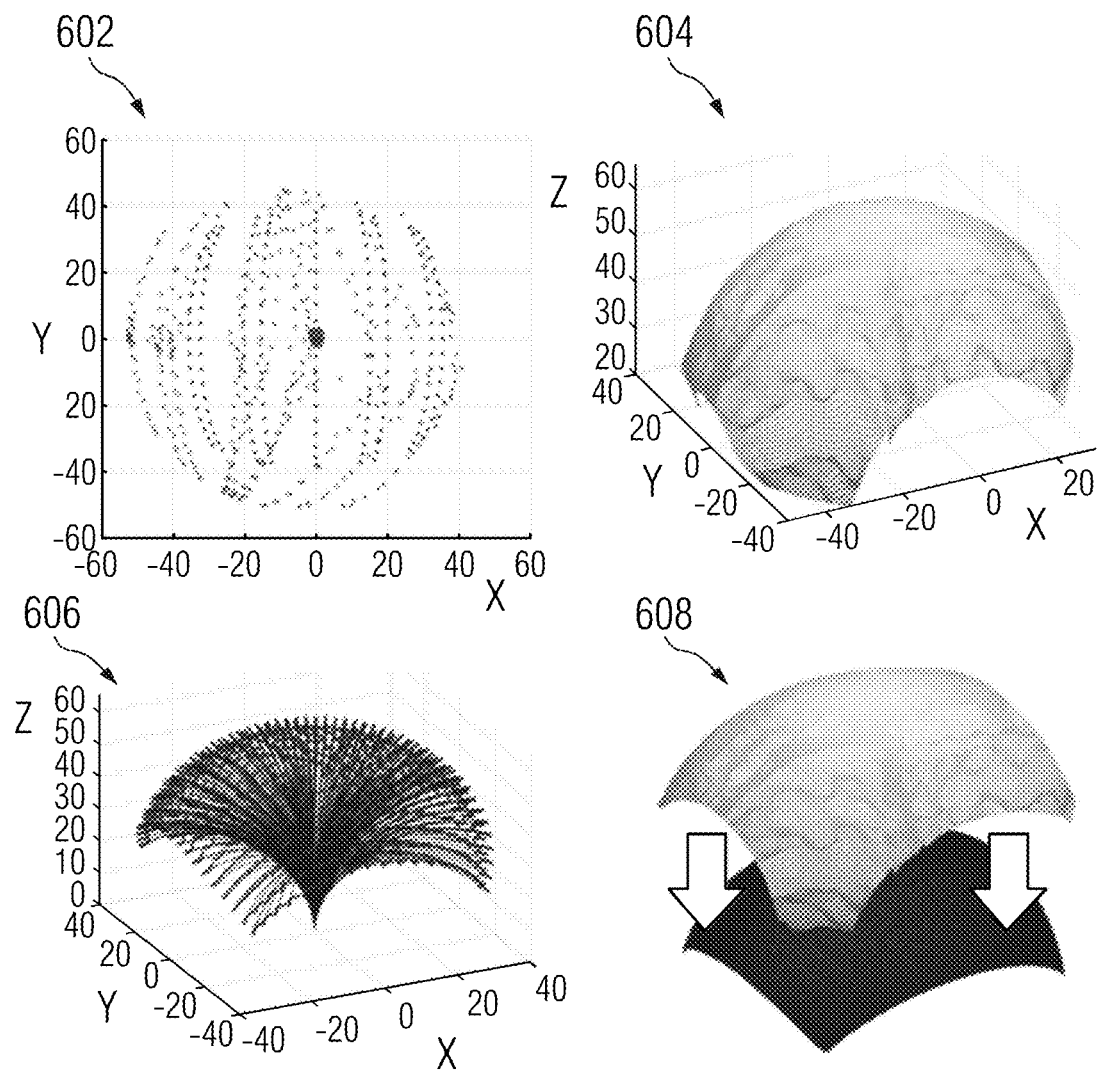
FIG. 6 shows graphs depicting non-linear elasticity compensation, in accordance with one or more embodiments.

Non-linear elasticity compensation is performed as follows. First, the model is conditioned by collecting ground truth data by manipulating the catheter by robot control and sampling the joint state ($\phi_1$, $\phi_2$) and the real position $P_{tip}$. This results in S number of samples, which give the real positions $P_{tip}$ related to ($\phi_1, \phi_2$). Referring to FIG. 6, graph 602 shows the bending plane X and Y comparing the sampled ground truth position $P_{tip}$ with the estimated position $\hat{P}_{tip}$. Second, let $P_j^* = (x_j^*, y_j^*, z_j^*)$ be the unobserved values based on the whole workspace ([-d,d]∈$\phi_1$ and $\phi_2$), where d is the maximum degree of knobs and j∈U, U is the number of unobserved values in the whole workspace. Then, a 2D interpolator is applied with collected data to estimate $P_j^*$. There are three interpolations: $(\emptyset_1^j, \emptyset_2^j) \rightarrow x_j^*$, $(\emptyset_1^j, \emptyset_2^j) \rightarrow y_j^*$ and $(\emptyset_1^j, \emptyset_2^j) \rightarrow z_j^*$. Graph 604 of FIG. 6 shows examples of interpolated $P^*$ corresponding to ($\phi_1, \phi_2$). Any suitable method for interpolation may be applied, such as, e.g., barycentric, polynomial, spline, etc. Third, the whole workspace inputs $(\emptyset_1^k, \emptyset_2^k)$, k∈S+U are applied into the forward kinematics model to determine $\hat{P}_{tip}^k$. Graph 606 of FIG. 6 shows the estimated position $\hat{P}_{tip}^k$ corresponding to ($\phi_1, \phi_2$). Lastly, the query position $\hat{P}_{tip}^k$ is picked and the nearest position in $P^* + P_{tip}$ is found. Then, a mapping function (e.g., a lookup table) is generated based on the determined nearest positions to map $(\emptyset_1^k, \emptyset_2^k) \rightarrow \hat{P}_{tip}^k$ and $\hat{P}_{tip}^k \rightarrow P^* + P_{tip}$, thus $P^* + P_{tip}$ gives the corrected values ($\phi_1'$, $\phi_2'$) corresponding to $(\emptyset_1^k, \emptyset_2^k)$. Graph 608 of FIG. 6 shows the real geometry in graph 604 mapped into the model geometry in graph 606.

Returning to step 404 of FIG. 4, in another embodiment, the configuration of the robotic catheter navigation system comprises a configuration of left/right parameter anterior/posterior parameter $\phi_2$, rotation parameter $\phi_3$, and distance parameter $d_4$ of the robotic catheter navigation system for rotating the catheter for navigating the catheter. Once the catheter is inside the heart (or any other anatomical object of interest) of the patient, an artificial intelligence algorithm is applied to automatically detect the relative position of the heart with respect to the catheter. Let $M_{heart}$ be the transformation matrix that aligns a point P in the image with the heart coordinate system $O_{heart}$, whose axes are aligned with longitudinal axis $e_l$, left ventricle/right ventricle axis $e_R$, and $e_l \hat{} e_R$. Further, let $M_{transducer}$ be the transformation matrix that aligns a point P in the image with the coordinate system of the transducer mounted on the catheter. The (X,Y,Z) Cartesian coordinates input by the user in the heart coordinate system $O_{heart}$ are transformed into the parameters $\phi_1$, $\phi_2$, $\phi_3$, $d_4$ of the robotic catheter navigation system by applying the inverse of the transformations M heart and M transducer and by applying the inverse kinematics model $f^{-1}$ of the catheter. In this way, a user control imaging directly from the heart coordinate system, achieving hand-eye coordination and a more intuitive navigation inside the cardiac chambers.

At step 406, the configuration is applied to the robotic catheter navigation system to automatically steer the catheter.

At step 408, optionally, an image of a view of the automatically steered catheter is generated and the generated image is output. For example, the generated image can be output by displaying the generated image on a display device of a computer system, storing the generated image on a memory or storage of a computer system, or by transmitting the generated image to a remote computer system.

In one embodiment, method 400 may be continuously repeated each time instructions are received for steering a catheter for imaging the patient (e.g., for performing an ICE procedure).

In one embodiment, method 200 of FIG. 2 may be performed after step 406 for automatic view recovery.

In one embodiment, given the forward kinematics model f of the catheter and the inverse kinematics model $f^{-1}$ of the catheter, many different intuitive interactions may be implemented. In one example, navigation from within the heart (or any other anatomical object of interest) of the patient may be implemented based on the kinematics models using augmented reality or virtual reality to allow for an immersive experience. Such a setup may be helpful for planning complex procedures, facilitating decision making, etc. In another example, a pose of object of interest (e.g., a medical device or an anatomical object of interest) in the patient may be identified and the robotic catheter navigation system may be configured to automatically steer the catheter with respect to the coordinate system associated with the object of interest. This would allow, for example, a user to quickly check for abnormalities along the devices by moving up and down, or would allow the catheter to maintain the object of interest in the center of its field of view.

In one embodiment, the robotic catheter navigation system may be configured for vision-based catheter control assisted steering. An object of interest (e.g., a medical device or an anatomical object of interest) in the patient may be identified and tracked in the images of the robotic catheter navigation system using, for example, an artificial intelligence based algorithm. The robotic catheter navigation system may be configured to steer the catheter based on the tracked object of interest. In one embodiment, the robotic catheter navigation system may steer the catheter based on the tracked object of interest to compensate for motion of the object of interest (e.g., due to breathing, heartbeat, etc.) to maintain the object of interest in the field of view. In another embodiment, the robotic catheter navigation system may be configured to automatically steer the catheter to generate a plurality of different points of view of the object of interest.

In one embodiment, the robotic catheter navigation system may be configured for detection of safety concerns. A 360 degree sweep may be performed (e.g., at regular, predefined intervals) for scanning the heart (or any other anatomical object of interest) of the patient. Safety concerns (e.g., thrombosis, pericardial effusion, etc.) may be automatically detected in the resulting images, e.g., using artificial intelligence based algorithms.

While the present invention is described with respect to various embodiments, it should be understood that features and advantages described with respect to one embodiment may apply equally to other embodiments. Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems using artificial intelligence based algorithms, as well as with respect to methods and systems for training artificial intelligence based algorithms. Features, advantages or alternative embodiments herein can be assigned to the other claimed objects and vice versa. In other words, claims for methods and systems for training artificial intelligence based algorithms can be improved with features described or claimed in context of the methods and systems for utilizing trained artificial intelligence based algorithms, and vice versa.

In particular, the trained artificial intelligence based algorithms can be adapted by the methods and systems for training the artificial intelligence based algorithms. Furthermore, the input data of the trained artificial intelligence based algorithms can comprise advantageous features and embodiments of the training input data, and vice versa. Furthermore, the output data of the trained artificial intelligence based algorithms can comprise advantageous features and embodiments of the output training data, and vice versa.

In general, a trained artificial intelligence based algorithms mimics cognitive functions that humans associate with other human minds. In particular, by training based on training data, the trained machine learning based network is able to adapt to new circumstances and to detect and extrapolate patterns.

In general, parameters of an artificial intelligence based algorithm can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained artificial intelligence based algorithm can be adapted iteratively by several steps of training.

In particular, a trained artificial intelligence based algorithm can comprise a machine learning based network, such as, e.g., a neural network, a support vector machine, a decision tree, and/or a Bayesian network, and/or the trained artificial intelligence based algorithm can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 7:
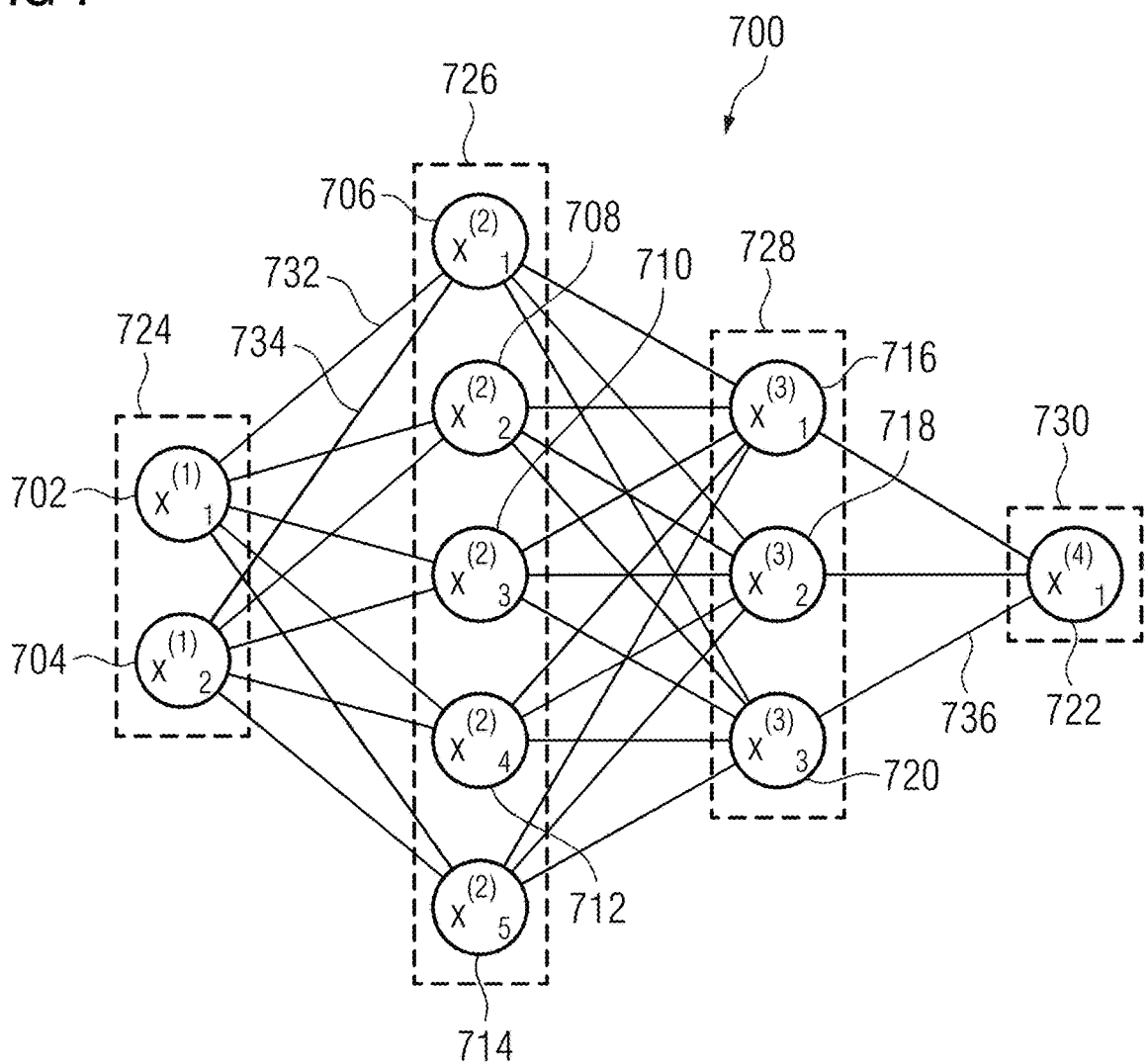
FIG. 7 shows an exemplary artificial neural network that may be used to implement one or more embodiments.

FIG. 7 shows an embodiment of an artificial neural network 700, in accordance with one or more embodiments. Alternative terms for "artificial neural network" are "neural network", "artificial neural net" or "neural net". Machine learning networks described herein may be implemented using artificial neural network 700.

The artificial neural network 700 comprises nodes 702-722 and edges 732, 734, . . . , 736, wherein each edge 732, 734, . . . , 736 is a directed connection from a first node 702-722 to a second node 702-722. In general, the first node 702-722 and the second node 702-722 are different nodes 702-722, it is also possible that the first node 702-722 and the second node 702-722 are identical. For example, in FIG. 7, the edge 732 is a directed connection from the node 702 to the node 706, and the edge 734 is a directed connection from the node 704 to the node 706. An edge 732, 734, . . . , 736 from a first node 702-722 to a second node 702-722 is also denoted as "ingoing edge" for the second node 702-722 and as "outgoing edge" for the first node 702-722.

In this embodiment, the nodes 702-722 of the artificial neural network 700 can be arranged in layers 724-730, wherein the layers can comprise an intrinsic order introduced by the edges 732, 734, . . . , 736 between the nodes 702-722. In particular, edges 732, 734, . . . , 736 can exist only between neighboring layers of nodes. In the embodiment shown in FIG. 7, there is an input layer 724 comprising only nodes 702 and 704 without an incoming edge, an output layer 730 comprising only node 722 without outgoing edges, and hidden layers 726, 728 in-between the input layer 724 and the output layer 730. In general, the number of hidden layers 726, 728 can be chosen arbitrarily. The number of nodes 702 and 704 within the input layer 724 usually relates to the number of input values of the neural network 700, and the number of nodes 722 within the output layer 730 usually relates to the number of output values of the neural network 700.

In particular, a (real) number can be assigned as a value to every node 702-722 of the neural network 700. Here, $x^{(n)}_i$ denotes the value of the i-th node 702-722 of the n-th layer 724-730. The values of the nodes 702-722 of the input layer 724 are equivalent to the input values of the neural network 700, the value of the node 722 of the output layer 730 is equivalent to the output value of the neural network 700. Furthermore, each edge 732, 734, . . . , 736 can comprise a weight being a real number, in particular, the weight is a real number within the interval [−1, 1] or within the interval [0, 1]. Here, $w^{(m,n)}_{i,j}$ denotes the weight of the edge between the i-th node 702-722 of the m-th layer 724-730 and the j-th node 702-722 of the n-th layer 724-730. Furthermore, the abbreviation $w^{(n)}_{i,j}$ is defined for the weight $w^{(n,n+1)}_{i,j}$.

In particular, to calculate the output values of the neural network 700, the input values are propagated through the neural network. In particular, the values of the nodes 702-722 of the (n+1)-th layer 724-730 can be calculated based on the values of the nodes 702-722 of the n-th layer 724-730 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions The transfer function is mainly used for normalization purposes.

In particular, the values are propagated layer-wise through the neural network, wherein values of the input layer 724 are given by the input of the neural network 700, wherein values of the first hidden layer 726 can be calculated based on the values of the input layer 724 of the neural network, wherein values of the second hidden layer 728 can be calculated based in the values of the first hidden layer 726, etc.

In order to set the values $w^{(m,n)}_{i,j}$ for the edges, the neural network 700 has to be trained using training data. In particular, training data comprises training input data and training output data (denoted as $t_i$). For a training step, the neural network 700 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 700 (backpropagation algorithm). In particular, the weights are changed according to $$w'^{(n)}_{i,j}=w^{(n)}_{i,j}-\gamma\cdot\delta^{(n)}_j\cdot x^{(n)}_i$$

wherein $\gamma$ is a learning rate, and the numbers $\delta^{(n)}_j$ can be recursively calculated as $$\delta^{(n)}_j=(\Sigma_k\delta^{(n+1)}_k\cdot w^{(n+1)}_{j,k})\cdot f'(\Sigma_i x^{(n)}_i\cdot w^{(n)}_{i,j})$$

based on $\delta^{(n+1)}_j$, if the (n+1)-th layer is not the output layer, and $$\delta^{(n)}_j=(x^{(n+1)}_k-t^{(n+1)}_j)\cdot f'(\Sigma_i x^{(n)}_i\cdot w^{(n)}_{i,j})$$

if the (n+1)-th layer is the output layer 730, wherein f' is the first derivative of the activation function, and $y^{(n+1)}_j$ is the comparison training value for the j-th node of the output layer 730.

Figure 8:
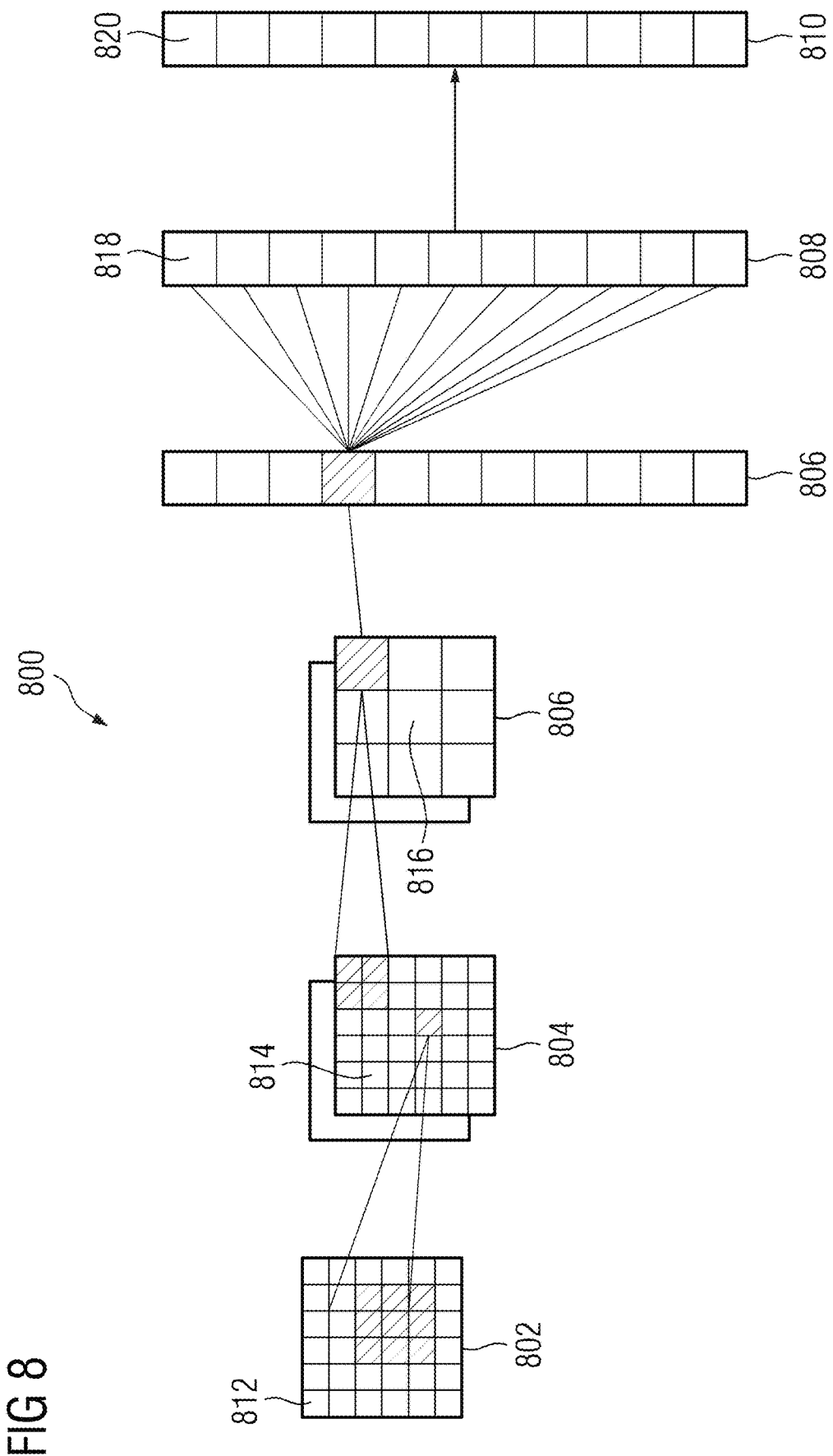
FIG. 8 shows a convolutional neural network that may be used to implement one or more embodiments.

FIG. 8 shows a convolutional neural network 800, in accordance with one or more embodiments. Machine learning networks described herein may be implemented using convolutional neural network 800.

In the embodiment shown in FIG. 8, the convolutional neural network comprises 800 an input layer 802, a convolutional layer 804, a pooling layer 806, a fully connected layer 808, and an output layer 810. Alternatively, the convolutional neural network 800 can comprise several convolutional layers 804, several pooling layers 806, and several fully connected layers 808, as well as other types of layers. The order of the layers can be chosen arbitrarily, usually fully connected layers 808 are used as the last layers before the output layer 810.

In particular, within a convolutional neural network 800, the nodes 812-820 of one layer 802-810 can be considered to be arranged as a d-dimensional matrix or as a d-dimensional image. In particular, in the two-dimensional case the value of the node 812-820 indexed with i and j in the n-th layer 802-810 can be denoted as $x^{(n)}_{[i,j]}$. However, the arrangement of the nodes 812-820 of one layer 802-810 does not have an effect on the calculations executed within the convolutional neural network 800 as such, since these are given solely by the structure and the weights of the edges.

In particular, a convolutional layer 804 is characterized by the structure and the weights of the incoming edges forming a convolution operation based on a certain number of kernels. In particular, the structure and the weights of the incoming edges are chosen such that the values $x^{(n)}_k$ of the nodes 814 of the convolutional layer 804 are calculated as a convolution $x^{(n)}_k=K_k*x^{(n-1)}$ based on the values $x^{(n-1)}$ of the nodes 812 of the preceding layer 802, where the convolution * is defined in the two-dimensional case as $$x^{(n)}_k[i,j]=(K_k*x^{(n-1)})[i,j]=\Sigma_{i'}\Sigma_{j'}K_k[i',j']\cdot x^{(n-1)}[i-i',j-j'].$$

Here the k-th kernel $K_k$ is a d-dimensional matrix (in this embodiment a two-dimensional matrix), which is usually small compared to the number of nodes 812-818 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 812-820 in the respective layer 802-810. In particular, for a convolutional layer 804, the number of nodes 814 in the convolutional layer is equivalent to the number of nodes 812 in the preceding layer 802 multiplied with the number of kernels.

If the nodes 812 of the preceding layer 802 are arranged as a d-dimensional matrix, using a plurality of kernels can be interpreted as adding a further dimension (denoted as "depth" dimension), so that the nodes 814 of the convolutional layer 804 are arranged as a (d+1)-dimensional matrix. If the nodes 812 of the preceding layer 802 are already arranged as a (d+1)-dimensional matrix comprising a depth dimension, using a plurality of kernels can be interpreted as expanding along the depth dimension, so that the nodes 814 of the convolutional layer 804 are arranged also as a (d+1)-dimensional matrix, wherein the size of the (d+1)-dimensional matrix with respect to the depth dimension is by a factor of the number of kernels larger than in the preceding layer 802.

The advantage of using convolutional layers 804 is that spatially local correlation of the input data can exploited by enforcing a local connectivity pattern between nodes of adjacent layers, in particular by each node being connected to only a small region of the nodes of the preceding layer.

In embodiment shown in FIG. 8, the input layer 802 comprises 36 nodes 812, arranged as a two-dimensional 6×6 matrix. The convolutional layer 804 comprises 72 nodes 814, arranged as two two-dimensional 6×6 matrices, each of the two matrices being the result of a convolution of the values of the input layer with a kernel. Equivalently, the nodes 814 of the convolutional layer 804 can be interpreted as arranges as a three-dimensional 6×6×2 matrix, wherein the last dimension is the depth dimension.

A pooling layer 806 can be characterized by the structure and the weights of the incoming edges and the activation function of its nodes 816 forming a pooling operation based on a non-linear pooling function f. For example, in the two dimensional case the values $x^{(n)}$ of the nodes 816 of the pooling layer 806 can be calculated based on the values $x^{(n-1)}$ of the nodes 814 of the preceding layer 804 as $$x^{(n)}[i,j]=f(x^{(n-1)}[id_1,jd_2],\ldots,x^{(n-1)}[id_1+d_1-1,jd_2+d_2-1])$$

In other words, by using a pooling layer 806, the number of nodes 814, 816 can be reduced, by replacing a number $d_1\cdot d_2$ of neighboring nodes 814 in the preceding layer 804 with a single node 816 being calculated as a function of the values of said number of neighboring nodes in the pooling layer. In particular, the pooling function f can be the max-function, the average or the L2-Norm. In particular, for a pooling layer 806 the weights of the incoming edges are fixed and are not modified by training.

The advantage of using a pooling layer 806 is that the number of nodes 814, 816 and the number of parameters is reduced. This leads to the amount of computation in the network being reduced and to a control of overfitting.

In the embodiment shown in FIG. 8, the pooling layer 806 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 808 can be characterized by the fact that a majority, in particular, all edges between nodes 816 of the previous layer 806 and the nodes 818 of the fully-connected layer 808 are present, and wherein the weight of each of the edges can be adjusted individually.

In this embodiment, the nodes 816 of the preceding layer 806 of the fully-connected layer 808 are displayed both as two-dimensional matrices, and additionally as non-related nodes (indicated as a line of nodes, wherein the number of nodes was reduced for a better presentability). In this embodiment, the number of nodes 818 in the fully connected layer 808 is equal to the number of nodes 816 in the preceding layer 806. Alternatively, the number of nodes 816, 818 can differ.

Furthermore, in this embodiment, the values of the nodes 820 of the output layer 810 are determined by applying the Softmax function onto the values of the nodes 818 of the preceding layer 808. By applying the Softmax function, the sum the values of all nodes 820 of the output layer 810 is 1, and all values of all nodes 820 of the output layer are real numbers between 0 and 1.

A convolutional neural network 800 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 800 can be trained based on the backpropagation algorithm. For preventing overfitting, methods of regularization can be used, e.g. dropout of nodes 812-820, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2 and 4. Certain steps or functions of the methods and workflows described herein, including one or more of the steps or functions of FIGS. 2 and 4, may be performed by a server or by another processor in a network-based cloud-computing system. Certain steps or functions of the methods and workflows described herein, including one or more of the steps of FIGS. 2 and 4, may be performed by a client computer in a network-based cloud computing system. The steps or functions of the methods and workflows described herein, including one or more of the steps of FIGS. 2 and 4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2 and 4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 9:
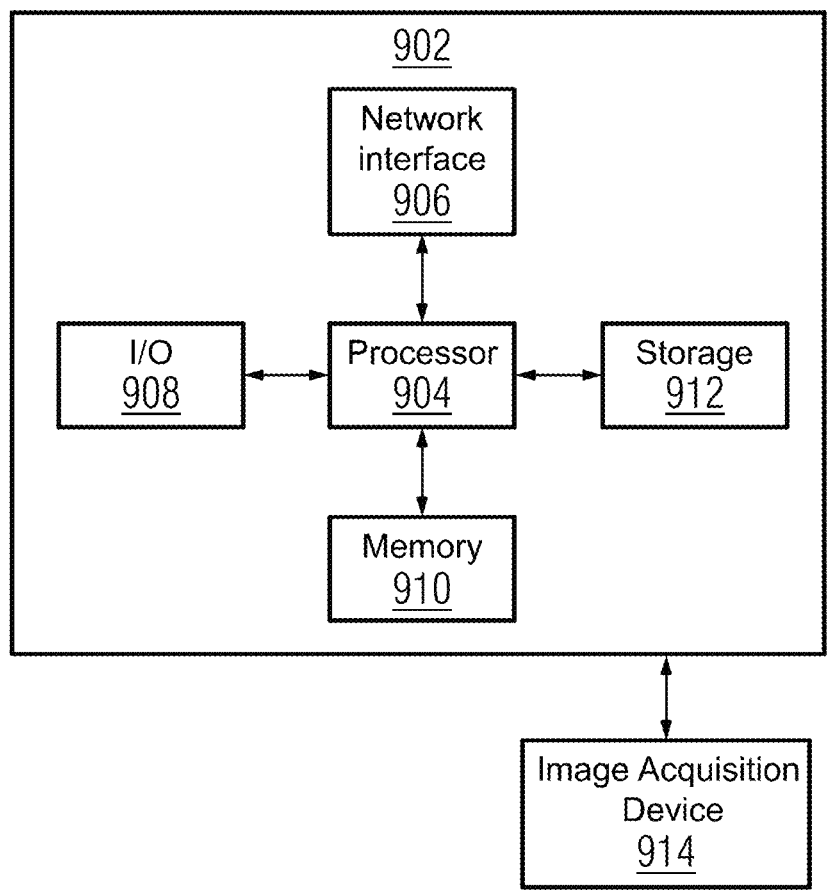
FIG. 9 shows a high-level block diagram of a computer that may be used to implement one or more embodiments.

A high-level block diagram of an example computer 902 that may be used to implement systems, apparatus, and methods described herein is depicted in FIG. 9. Computer 902 includes a processor 904 operatively coupled to a data storage device 912 and a memory 910. Processor 904 controls the overall operation of computer 902 by executing computer program instructions that define such operations. The computer program instructions may be stored in data storage device 912, or other computer readable medium, and loaded into memory 910 when execution of the computer program instructions is desired. Thus, the method and workflow steps or functions of FIG. 2 can be defined by the computer program instructions stored in memory 910 and/or data storage device 912 and controlled by processor 904 executing the computer program instructions. For example, the computer program instructions can be implemented as computer executable code programmed by one skilled in the art to perform the method and workflow steps or functions of FIGS. 2 and 4. Accordingly, by executing the computer program instructions, the processor 904 executes the method and workflow steps or functions of FIGS. 2 and 4. Computer 902 may also include one or more network interfaces 906 for communicating with other devices via a network. Computer 902 may also include one or more input/output devices 908 that enable user interaction with computer 902 (e.g., display, keyboard, mouse, speakers, buttons, etc.).

Processor 904 may include both general and special purpose microprocessors, and may be the sole processor or one of multiple processors of computer 902. Processor 904 may include one or more central processing units (CPUs), for example. Processor 904, data storage device 912, and/or memory 910 may include, be supplemented by, or incorporated in, one or more application-specific integrated circuits (ASICs) and/or one or more field programmable gate arrays (FPGAs).

Data storage device 912 and memory 910 each include a tangible non-transitory computer readable storage medium. Data storage device 912, and memory 910, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 908 may include peripherals, such as a printer, scanner, display screen, etc. For example, input/output devices 908 may include a display device such as a cathode ray tube (CRT) or liquid crystal display (LCD) monitor for displaying information to the user, a keyboard, and a pointing device such as a mouse or a trackball by which the user can provide input to computer 902.

An image acquisition device 914 can be connected to the computer 902 to input image data (e.g., medical images) to the computer 902. It is possible to implement the image acquisition device 914 and the computer 902 as one device. It is also possible that the image acquisition device 914 and the computer 902 communicate wirelessly through a network. In a possible embodiment, the computer 902 can be located remotely with respect to the image acquisition device 914.

Any or all of the systems and apparatus discussed herein, such as, e.g., controller 118 of FIG. 1, may be implemented using one or more computers such as computer 902.

One skilled in the art will recognize that an implementation of an actual computer or computer system may have other structures and may contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
receiving instructions for steering a catheter within a patient;
transforming the received instructions into a configuration of a robotic catheter navigation system;
collecting ground truth positions of the catheter;
interpolating the ground truth positions of the catheter to generate unobserved positions of the catheter;
determining nearest positions between the ground truth positions and the unobserved positions;
generating a mapping function based on the determined nearest positions;
compensating the transformation based on the mapping function; and
applying the configuration to the robotic catheter navigation system to automatically steer the catheter within the patient.

2. The method of claim 1, wherein the configuration defines a position and orientation of the catheter.

3. The method of claim 2, wherein the position is defined by a translation parameter and the orientation is defined by rotation, anterior/posterior, and left/right parameters.

4. The method of claim 1, wherein receiving instructions for steering a catheter within a patient comprises:
receiving the instructions in a coordinate system associated with the patient for steering the catheter.

5. The method of claim 1, wherein transforming the received instructions into a configuration of a robotic catheter navigation system comprises:
transforming the received instructions into the configuration of the robotic catheter navigation system based on a kinematics model of the catheter.

6. An apparatus comprising:
means for receiving instructions for steering a catheter within a patient;
means for transforming the received instructions into a configuration of a robotic catheter navigation system;
means for collecting ground truth positions of the catheter;
means for interpolating the ground truth positions of the catheter to generate unobserved positions of the catheter;
means for determining nearest positions between the ground truth positions and the unobserved positions;
means for generating a mapping function based on the determined nearest positions;
means for compensating the transformation based on the mapping function; and means for applying the configuration to the robotic catheter navigation system to automatically steer the catheter within the patient.

7. The apparatus of claim 6, wherein the configuration defines a position and orientation of the catheter.

8. The apparatus of claim 7, wherein the position is defined by a translation parameter and the orientation is defined by rotation, anterior/posterior, and left/right parameters.

9. A non-transitory computer readable medium storing computer program instructions, the computer program instructions when executed by a processor cause the processor to perform operations comprising:
receiving instructions for steering a catheter within a patient;
transforming the received instructions into a configuration of a robotic catheter navigation system;
collecting ground truth positions of the catheter;
interpolating the ground truth positions of the catheter to generate unobserved positions of the catheter;
determining nearest positions between the ground truth positions and the unobserved positions;
generating a mapping function based on the determined nearest positions;
compensating the transformation based on the mapping function; and
applying the configuration to the robotic catheter navigation system to automatically steer the catheter within the patient.

10. The non-transitory computer readable medium of claim 9, wherein receiving instructions for steering a catheter within a patient comprises:
receiving the instructions in a coordinate system associated with the patient for steering the catheter.

11. The non-transitory computer readable medium of claim 9, wherein transforming the received instructions into a configuration of a robotic catheter navigation system comprises:
transforming the received instructions into the configuration of the robotic catheter navigation system based on a kinematics model of the catheter.

12. The apparatus of claim 6, wherein the means for receiving instructions for steering a catheter within a patient comprises:
means for receiving the instructions in a coordinate system associated with the patient for steering the catheter.

13. The apparatus of claim 6, wherein the means for transforming the received instructions into a configuration of a robotic catheter navigation system comprises:
means for transforming the received instructions into the configuration of the robotic catheter navigation system based on a kinematics model of the catheter.

14. The non-transitory computer readable medium of claim 9, wherein the configuration defines a position and orientation of the catheter.

15. The non-transitory computer readable medium of claim 14, wherein the position is defined by a translation parameter and the orientation is defined by rotation, anterior/posterior, and left/right parameters.

* * * * *